Figure 1:
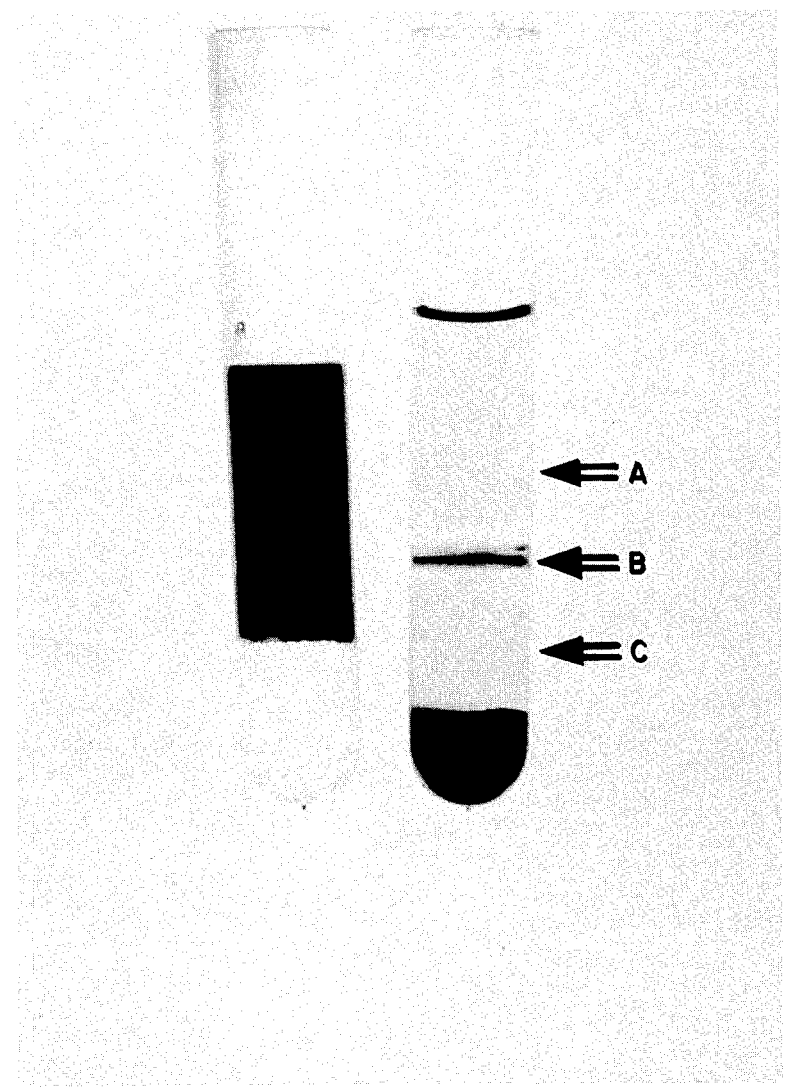

United States Patent [19]

Burns et al.

[11] Patent Number: 4,822,745

[45] Date of Patent: Apr. 18, 1989

[54] METHOD FOR QUANTIFYING HUMAN RETICULOCYTES

[75] Inventors: Edward R. Burns, Flushing; Barry Wenz, White Plains; Shraga N. Goldberg, Flushing, all of N.Y.

[73] Assignee: Albert Einstein College of Medicine of Yeshiva University, Bronx, N.Y.

[21] Appl. No.: 938,547

[22] Filed: Dec. 5, 1986

[51] Int. Cl.$^4$ .................... G01N 33/48; G01N 35/00; G01N 35/02

[52] U.S. Cl. ...................................... 436/63; 436/45; 436/47

[58] Field of Search ...................... 422/44; 436/45, 47, 436/63; 377/10; 424/101

[56] References Cited

PUBLICATIONS

Brecher, G., and Schneiderman, M.: A Time Saving Device for the Counting of Reticulocytes, Am. J. Clin. Pathol., 1950; 20:1079–1083.

Corash, L., Klein, L., Deisseroth, A., et al.: Selective Isolation of Young Erythrocytes for Transfusion Support of Thalassemia Major Patients, Blood, 1981; 57:599.

Corash, L. M., Piomelli, S., Chen, H. C., Seaman, C., and Gross, E.: Separation of Erythrocytes According to Age on a Simplified Density Gradient, J. Lab. Clin. Med., 1974; 84:147–151.

Fabry, M. E., and Nagel, R. L.: Heterogeneity of Red Cells in the Sickler: A Characteristic with Practical Clinical and Pathophysiologic Implications, Blood Cells, 1982; 8:9–15.

Herz, F., Kaplan, E., and Scheye, E. S.: Diagnosis of Erythrocytes Glucose –6 Phosphate Dehydrogenase Deficiency in Negro Male Despite Hemolytic Crisis, Blood, 1970; 35:90.

Leif, R. C. and Vinograd, J.: The Distribution of Buoyant Density of Human Erythrocytes in Bovine Albumin Solutions, Proc. Natl. Acad. Sci., 1964; 51:520–528.

May, J. A. and Sage, B. H.: Spinner Films for Reticulocyte Counts, Am. J. Med. Technol., 1976; 42:357–360.

Motulsky, A. G., and Yoshida, A.: Methods for the Study of Red Cell Glucose –6 Phosphate Dehydrogenase, in Biomedical Methods in Red Cell Genetics, ed. J. J. Yunis, New York: Academic Press, 1969, pp. 51–93.

Nelson, D. A.: Hematology and Coagulation, in Clinical Diagnosis and Management by Laboratory Methods, Edited by J. B. Henry, Philadelphia, W. B. Saunders, 1979, pp. 888–889.

Peebles, D. A., Hochberg, A., and Clark, T. D.: Analysis of Manual Reticulocyte Counting, Am. J. Clin. Pathol., 1981; 76:713–717.

Savage, R. A., Skoog, D. P., and Rabinovitch, A.: Analytic Inaccuracy and Imprecision in Reticulocyte Counting: A Preliminary Report from the College of American Pathologists Reticulocyte Project, Blood Cells, 1985; 11:97–112.

Tanke, H. J., Rothbarte, P. H., Vossen, J. M. J. J., Koper, G. J., and Ploem, J. S.: Flow Cytometry of Reticulocytes Applied to Clinical Hematology, Blood, 1983; 61:1091–1097.

Vander, J. B., Harris, C. A. and Ellis, S. R.: Reticulocyte Counts by Means of Fluorescence Microscopy, J. Lab. Clin. Med., 1963; 62:132.

Vaughan, W. P., Hall, J., Dougherty, C., Peebles, D.: Simultaneous Reticulocyte and Platelet Counting on a Clinical Flow Cytometer, Am. J. Hematol., 1985; 18:385–391.

Primary Examiner—Frederick E. Waddell
Attorney, Agent, or Firm—Amster, Rothstein & Ebenstein

[57] ABSTRACT

A method for determining the reticulocyte population in a blood sample includes the steps of determining the average cell size of the blood sample, partitioning the sample by centrifugation through a medium of known density so as to provide a fraction enriched with neocytes, determining the average cell size of the fraction, comparing the average cell size of the sample to the average cell size of the fraction and utilizing this comparison to provide a determination of the population of reticulocytes in the sample.

16 Claims, 3 Drawing Sheets

FIG. I

METHOD FOR QUANTIFYING HUMAN RETICULOCYTES

The invention relates to a method for quantifying human reticulocytes in a blood sample by sizing the sample and a fraction of the sample enriched for neocytes.

The corrected reticulocyte count provides for an indirect but simple means of assessing erythrocyte production. The conventional technique requires blood to be stained with a supravital dye (a dye specific for reticulocytes), and a smeared film of the stained blood to be examined microscopically. The selective staining of RNA reticulum allows the reticulocyte population to be identified and quantified. Despite the method's widespread use, it is time consuming and inherently imprecise due to the quantification of a relatively small cell cohort. For example, performing a reticulocyte estimate by surveying 1000 red blood cells (RBC) containing a 1% subpopulation of reticulocytes, yields data with $\pm 60\%$ error. A 10% reticulocyte count is subject to a $\pm 19\%$ error. Since the normal reticulocyte population is from 1 to 3% of all red blood cells, this degree of imprecision obviously limits the utility of the assay, and precludes its ability to detect significant changes in erythropoesis. Imprecision is compounded by other sources of error including: non random distribution of reticulocytes in a blood film, and interobserver bias. The latter difficulty most commonly occurs with Heilmeyer Stage IV mature reticulocytes.

Methods which circumvent these problems have been previously described. Among these are the use of pattern recognition devices which identify and quantitate reticulocytes using specifically prepared and stained blood smears and the use of flow cytometers, which identify the reticulocyte by tagging its RNA with fluorescent dyes such as acridine orange or pyronin Y. These automated and objective techniques markedly improve the precision of the reticulocyte count. However, they require the availability of capital equipment which generally cannot be solely justified for the performance of this low volume assay.

Accordingly, it is an object of the present invention to provide an accurate and precise method for quantifying human reticulocytes.

Another object of the present invention is to provide a reproducible method for quantifying reticulocytes which removes the subjectivity and potential for operator error inherent in prior art methods.

Still another object of the present invention is to provide a method for quantifying reticulocytes which utilizes materials and equipment which are readily available in clinical hematology laboratories and therefore can be readily and inexpensively practiced.

A further object of the present invention is to provide a method for quantifying reticulocytes which is not as labor intensive as prior art techniques and which is capable of batch analysis.

A still further object of the present invention is to provide a method for quantifying reticulocytes which is cost effective, accurate and precise as compared to prior art methods.

In accordance with the above objectives, the present invention is a method for determining the population of reticulocytes in a blood sample which includes the steps of determining the average cell size of the sample, partitioning the sample by centrifugation through a medium of known density to provide a fraction enriched with neocytes, determining the average cell size of the fraction, comparing the average cell size to the sample to the average cell size of the fraction and utilizing this comparison to provide a determination of the population of reticulocytes in the sample.

Figure 2:
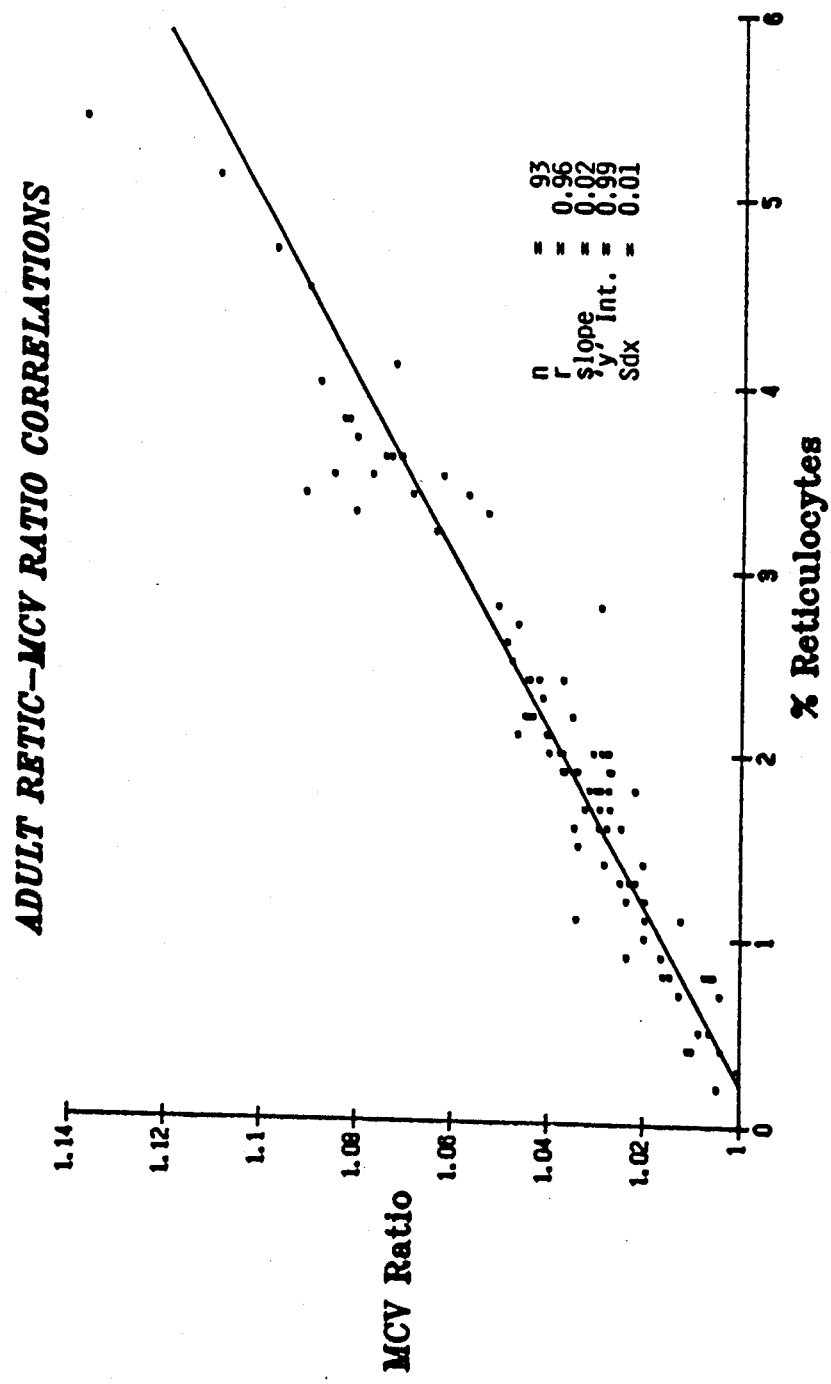
Figure 3:
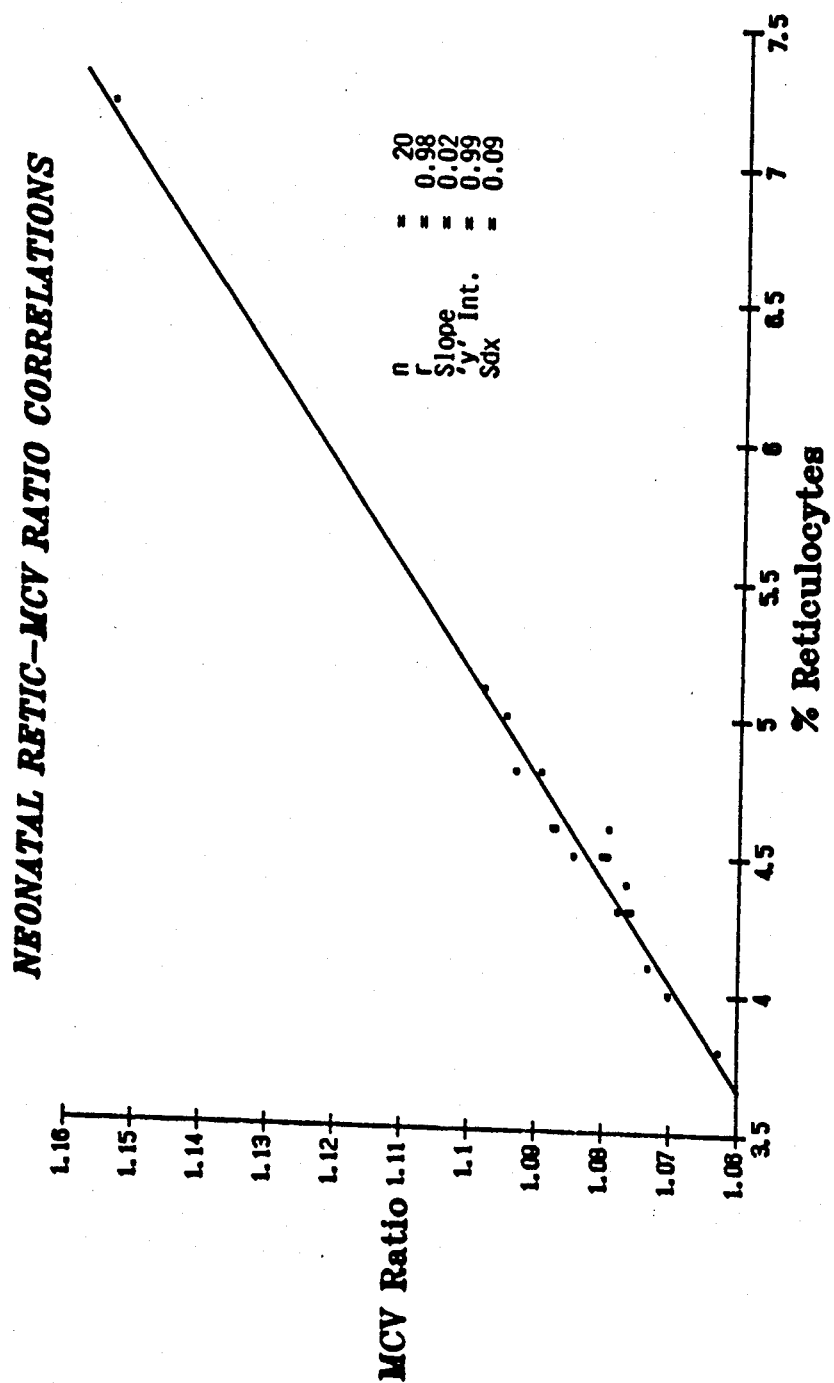

The above brief description as well as further objectives, features and advantages of the present invention will be more fully understood by reference to the following detailed description of the presently preferred, but nonetheless illustrative embodiments in accordance with the present invention, when taken in conjunction with the accompanying drawings, wherein:

FIG. 1 is an elevational view of a pair of test tubes, the tube on the left showing whole blood-layered on top of a medium of known density before centrifugation, and the tube on the right showing the post centrifugation fractionation of the blood;

FIG. 2 is a linear regression plot comparing results (reticulocyte percentage) obtained for adult samples with the method of the present invention to results obtained with conventional microscopic determination method; and FIG. 3 is a linear regression plot comparing results (reticulocyte percentage) obtained for neonatal samples with the method of the present invention to results obtained with conventional microscopic determination method.

The present invention is a method for quantifying reticulocytes based on their relatively unique size and buoyant density. The technique partitions whole bood by centrifugation through a medium of a known density (e.g., arabino-galactan polysaccharide-"Stractan"), and allows the sizing of the derived subpopulation of buoyant cells with a standard automated blood cell analyzer. The mean corpuscular volume ("MCV") obtained for the latter fraction is then compared to that of the whole blood sample to obtain a Stractan layer to whole blood MCV ratio, and by use of a standard curve an accurate reticulocyte estimation is achieved. Reticulocyte counts generated in this manner have greater precision than the conventional prior art methods, accommodate batch analysis and require minimal processing time.

More specifically, the invention utilizes a conventional clinical blood cell analyzer to size the red cell neocyte population of a blood sample, which population relates to the reticulocyte fraction in linear fashion (reticulocyte population is a large subset of the neocyte population). Blood is layered atop Stractan and centrifuged for 30 minutes at 1500 g. This density medium fractionation process enriches the Stractan layer with neocytes by up to twenty fold as determined by G6PD enzyme analysis (G6PD varies with cell age, younger cells have a higher level of the enzyme). The MCV of the red cells partitioning in the Stractan layer and the starting whole blood is measured. The ratio of the two MCV measurements is then related to the reticulocyte percentage by a standard curve. The use of the standard curve is possible since the derived MCV ratio is linearly correlated with manual reticulocyte counts.

In order to prepare the standard curve equating reticulocyte population to MCV ratio which is utilized in the method of the invention, whole blood aliquots anticoagulated with $K_3$ ethylenediaminetetracetate (EDTA) (1 ml: 1.5 mg) were incubated with equal volumes of New Methylene Blue solution for 10 minutes at room temperature. Blood films prepared from these specimens were examined microscopically and using a Miller optical disk, the reticulocyte percentage was estimated from the equivalent of 2,700 red cells. All counts were performed in duplicate. Results of this technique were accepted as the reference values for statistical comparisons. This procedure provided reticulocyte counts of various samples through use of the prior art counting technique described above. The MCV ratios of these samples were then determined by the method of the present invention.

Arabino-galactan polysaccharide (Stractan, available from the St. Regis Paper Co., West Nyack, N.Y.) with an osmolarity of 291 mosm/L was prepared as a stock solution according to standard methods, such as that described by Corash, et al. in the article "Separation of Erythrocytes According to Age on a Simplified Density Gradient," *J. Lab. Clin. Med.*, Vol. 84, pp. 147–151 (1974). The working solution was prepared from stock by dilution to a specific gravity of 1.089. Hematocrits, RBC counts and mean corpuscular volumes of whole blood samples were analyzed using a standard hematology analyzer, such as a Coulter S+IV (available from Coulter Electronics, Hialeah, Fla.) hematology analyzer. Prior to testing, all samples were adjusted to a hematocrit of 20% by removal of plasma or dilution with RPMI 1640 (available from GIBCO Laboratories, Grand Island, N.Y.) supplemented with 5% bovine serum albumin (available from Sigma, St. Louis, Mo.). Preliminary experiments demonstrated that the MCV of the red cells in the Stractan buoyant layer varies directly with the specimen's starting hematocrit, and that the precision of the test is greatest, a coefficient of variation ("C.V.") of 1%, with a hematocrit of 20%.

Referring now to FIG. 1 (left hand tube), a 2 ml. aliquot of the adjusted sample was layered atop 1 ml. of the Stractan solution in 75+12 mm plastic tubes (available from Sarstedt, West Germany) and centrifuged at 2,700 R.P.M. for 30 minutes in a Beckman TJ6 centrifuge equipped with a TH 4 swinging-bucket rotor (available from Beckman Instruments, Palo Alto, Calif.). Relative centrifugal field was 1,500 g (rotor radius of 11 cm).

Centrifugation consistently separates the whole blood sample into two distinct layers as shown by the right hand tube in FIG. 1. The upper layer consists of a thin band of red cells at the Stractan plasma interface (indicated by arrow A, the plasma is above the interface). In addition, the stractan medium itself contains a small percentage of the total red cell population uniformly suspended within the stractan medium giving it a uniform light red color (indicated by arrow B). This fraction (the plasma, the thin band of red cells at the Stractan plasma interface and the Stractan medium) is termed the Stractan layer. The bottom layer of the tube contains densely packed red cells (indicated by arrow C), which are not part of the Stractan layer. The Stractan layer is removed with a transfer pipette and gently mixed. The reticulocyte assay is performed by measuring the MCV of both the native blood (the initial blood sample prior to centrifugation) and the red blood cells contained in the Stractan layer. The ratio of these MCV measurements (Stractan:Native) yields linear data equivalent to the conventional reticulocyte count which can be read from a standard curve. The standard curve was constructed by linear regression analysis comparing the MCV ratio to the previously determined convantional reticulocyte count using specimens whose microscopically measured reticulocyte counts ranged from 0–6%.

The percentage or reticulocytes in the red blood cells confined to the Stractan layer is significantly enriched compared to the bottom layer of densely packed red blood cells (arrow C) and the native sample. In twelve samples processed at random, the reticulocyte count of the upper band cohort is 7.7±4.3%, compared to 2.0±1.3% for the native whole blood samples (p less than 0.001). Reticulocyte enrichnment of the upper layer ranges from 2 to 7 fold, and contains 15 to 43% of the reticulocytes present in the whole blood. The degree of enrichment varies with each patient.

Samples from 93 adult patients were studied in the manner described above. All samples were obtained as aliquots of routine specimens Their reticulocyte counts ranged from 0.8% to 6.0%. As represented in FIG. 2, correlation between these conventional counts and those measured using the described MCV ratios has an $r=0.96$ (correlations between the calculated and observed measurements are presented as Pearson's r value) and a y intercept of 0.99 (the y intercept indicates the bias of the correlation between conventional counts and those measured using MCV ratios). The agreement between individual specimens analyzed by both techniques was within a 0.2%. No consistent correlations were obtained between any other red cell index (i.e. RBC, MCV, red cell distribution width, mean corpuscular hemaglobin concentration) and the reticulocyte count.

Samples from 20 neonates were also studied. Their conventionally measured reticulocyte counts range from 4.0% to 7.5%. As represented in FIG. 3, reticulocyte correlations for both methods have an $r=0.98$ and a y intercept of 0.95.

Ten samples from patients with homozygous hemoglobin S (sickle cell anemia) were also studied. Reticulocyte count correlation measurements performed using blood obtained from patients with sickle cell anemia were poor, r less than 0.5, and the data produced by the method of this invention proves to be non-linear, excluding the creation of a standard curve.

The "within and between" run precision measurements of the described procedure are excellent with C.V.=1.0% and 0.5%, respectively. Longitudinal precision was assessed using fresh specimens obtained daily from 3 patients over 5 days. These samples demonstrated a C.V. less than 0.05%.

The influence of specimen storage on the technique was assessed by repetitively assaying 6 bloods, maintained at 4° C. for 18 hours. Imprecision measurement over this time period displayed a C.V. less than 5%.

Seven whole blood samples were fractionated by the density medium technique following which quantitative G6PD assays were performed on the native blood specimen and the reticulocyte enriched band of RBC in the Stractan layer. G6PD content varies with cell age. Younger cells have a higher level of the enzyme and therefore G6PD content can be used to determine whether a sample or fraction contains neocytes (young or new cells). There was a consistent enrichment of the Stractan layer with both reticulocytes and higher G6PD content for all samples, but no linear relationship between the increases of these parameters exists. Mean reticulocyte counts for the whole blood ranged fom 1.1 to 1.8% while those of the Stractan layer ranged between 11.7 and 76.3%. Mean reticulocyte enrichment of the Stractan layer was 38 fold (p=0.002; p is a measure of statistical significance as determined by Student's t-test).

G6PD content of the whole blood ranged from 2046 U/L to 4290 U/L packed cells while that of the Stractan layer were between 2112 U/L and 63,195 U/L packed cells. Mean G6PD enrichment was 6.3 fold ($p=0.04$).

The described method for quantitating reticulocytes is objective and precise. It is applicable to normal and the majority of anemic patients. It quantifies reticulocytes in adult and neonatal specimens. However, it is not applicable to patients with abnormally dense red cell populations such as those with sickle cell anemia. Measurements of within run and between run imprecision average less than 1%, which is minimally 20 fold greater than the presently used conventional microscopic procedure. Some of the considerations which limit the conventional reticulocyte count such as the influence of red cell transfusion prior to procuring the specimen are applicable here, as well. The assay is exquisitely sensitive to changes in the whole blood MCV and is therefore affected by influences that factitiously alter it.

Analysis of all of the parameters generated by the Coulter S+IV confirm that it is only the calculated MCV ratio (the MCV of the Stractan fraction divided by the MCV of the sample) which correlates with the conventional reticulocyte count. Previous investigators have shown that reticulocytes are less dense than most other red cells. Using linear density gradients comprised of bovine serum albumin, it has been demonstrated that reticulocytes segregate as a narrow band which contains the lightest population of RBC. Further, it has been shown that young cells, as judged by in-vivo iron labeling studies, also segregate with the reticulocyte cohort. Cell volume measurements demonstrated that the volume distributions of light, medium and heavy fractions are as heterogeneous as those of unfractionated cells; suggesting that cell size alone does not equate to cell density.

Isolation of young neocytes has been accomplished using their lighter density to segregate them from older cells G6PD content varies with cell age, younger cells having a higher level of the enzyme. Our finding of markedly increased G6PD content within the upper layer of the centrifuged bloods suggests strongly that the predominant cell population of this cohort is comprised of neocytes. The MCV ratio measurement thus reflects the neocyte population which, in turn, is linearly related to the percentage of reticulocytes.

The correlation between the MCV ratio and the reticulocyte count reflects the above set of facts. Whole blood contains a cell population which is heterogeneous with regard to cell size and age. Density gradient fractionation separates this population into one maintaining the original cell size versus frequency distribution but enriched with neocytes/reticulocytes. Since neocytes are larger than older red cells, a cell population enriched with neocytes will have a slightly larger MCV than a starting population of red cells prior to enrichment. The ratio of the MCV of the enriched population to that of the starting blood normalizes the heterogeneity of cell volume distributions of fractionated and unfractionated blood. The final result is a reflection of the percentage difference between an individual's light reticulocyte population and his unique whole blood reticulocyte value. This difference correlates well with the conventional microscopically measured whole blood reticulocyte count.

The inability to use the method of the present invention to quantify reticulocytes in patients with homozygous sickle cell anemia is a reflection of that group of patients' greater RBC heterogeneity and dense cell population. It is also known that the MCV derived for sickle cells using automated equipment can be inaccurate. The Coulter cell counter relies on the ability of red cells to elongate into proloid eliptocytes in a shear plane. MCV is then measured on these elliptocytes. Sickle cells have a decreased deformability and do not readily change shape. Therefore, the MCV readings are often inaccurate.

The method of the invention is accurate and highly precise. Standard error for the linear regressions performed with adult and neonatal blood are 0.01 and less than 0.1, respectively. Reticulocyte counts generated by this method require approximately 45 minutes of processing, of which less than five minutes requires technical labor. Using routinely available equipment the laboratory can perform up to 20 reticulocyte counts in less than one hour by batch analysis with a cost effectiveness, accuracy and precision previously unachievable.

As will be readily apparent to those skilled in the art, the invention may be used in other specific forms or for other purposes without departing from its spirit or central characteristics. The present embodiments are therefore to be considered as illustrative and not restrictive, the scope of the invention being indicated by the claims rather than by foregoing description, and all embodiments which come within the range of equivalence of the claims are intended to be embraced.

We claim:

1. A method for determining the reticulocyte population in a blood sample of a patient not having a hematological disease characterized by an abnormally dense red cell population, comprising the steps of:
   (a) determining the average cell size of the blood sample;
   (b) partitioning the sample by centrifugation through a medium of known density equal to a specific density of 1.089 so as to provide a fraction enriched with neocytes;
   (c) determining the average cell size of the fraction obtained in step (b); and
   (d) comparing the average cell size of the sample, determined in step (a), to the average cell size of the fraction, determined in step (c), and utilizing this comparison to provide a determination of the population of reticulocytes in the sample by correlating the comparison to a set of predetermined measurements of reticulocyte population and corresponding comparison values.

2. The method of claim 1 in which the medium of known density permits concentration of neocytes therein during centrifugation.

3. The method of claim 1 in which the medium of known density is arabino-galactan polysaccharide.

4. The method of claim 1 in which the determination of average cell size is made utilizing a blood cell analyzer to provide a measurement of mean corpuscular volume.

5. A method for quantifying the reticulocyte population in a blood sample of a patient not having a hematological disease characterized by an abnormally dense red cell population, comprising the steps of:
   (a) determining the means corpuscular volume of the sample;

(b) subjecting the sample to density medium fractionation utilizing a medium having a specific density of 1.089 to yield a fraction which is enriched with neocytes;

(c) determining the mean corpuscular volume of the fraction of step (b);

(d) comparing the mean corpuscular volume of the fraction, determined in step (c), to the mean corpuscular volume of the sample, determined in step (a), and utilizing this comparison to provide an indication of the reticulocyte population in the sample by correlating the comparison to a set of predetermined measurements of reticulocyte population and corresponding comparison values.

6. The method of claim 5 in which the density medium fractionation step utilizes a medium which permits concentration of neocytes therein during centrifugation.

7. The method of claim 5 in which the density medium fractionation step utilizes arabino-galactan polysaccharide.

8. A method for determining the reticulocyte population in a blood sample of a patient not having a hematological disease characterized by an abnormally dense red cell population, comprising the steps of:

(a) diluting the sample;

(b) determining the mean corpuscular volume of the sample;

(c) centrifuging the sample with a medium of known density equal to a specific density of 1.089 to provide a fraction enriched with neocytes;

(d) determining the mean corpuscular volume of the fraction of step (c);

(e) comparing the mean corpuscular volume of the sample to the mean corpuscular volume of the fraction and correlating this comparison to a standard set of measurements of reticulocyte population and corresponding mean corpuscular volume comparison values to achieve a determination of the reticulocyte population of the sample.

9. The method of claim 8 in which the medium of known density permits concentration of neocytes therein during centrifugation.

10. The method of claim 8 in which the medium of known density is arabino-galactan polysaccharide.

11. The method of claim 8 in which the determination of mean corpuscular volume is made utilizing a blood cell analyzer.

12. A method for determining the reticulocyte population in a blood sample of a patient not having a hematological disease characterized by an abnormally dense red cell population, comprising the steps of:

(a) determining the average cell size of the blood sample;

(b) determining the average cell size of a fraction of the sample having a specific density of 1.089; and (c) comparing the average cell size of the sample, determined in step (a), to the average cell size of the fraction, determined in step (b), and utilizing this comparison to provide a determination of the population of reticulocytes in the sample by correlating the comparison to a set of predetermined measurements of reticulocyte population and corresponding comparison values.

13. The method of claim 12 including the step of determining average cell size by utilizing a blood cell analyzer to provide a measurement of mean corpuscular volume.

14. The method of claim 12 including the step of determining the average cell size by the mean corpuscular volume.

15. The method of claim 12 including the step of diluting the sample prior to step (a).

16. The method of claim 12 including the step of partitioning the sample by centrifugation through a medium with a specific density of 1.089 to provide the fraction.

* * * * *